US011535269B2

(12) United States Patent
Kang et al.

(10) Patent No.: US 11,535,269 B2
(45) Date of Patent: Dec. 27, 2022

(54) APPARATUS AND METHOD FOR PROVIDING CUSTOMIZED MOBILITY DRIVING PATH USING BRAIN WAVE

(71) Applicants: Hyundai Motor Company, Seoul (KR); Kia Motors Corporation, Seoul (KR); SOOKMYUNG WOMEN'S UNIVERSITY INDUSTRY-ACADEMIC COOPERATION FOUNDATION, Seoul (KR)

(72) Inventors: Jeong Su Kang, Seongnam-si (KR); Suh Yeon Dong, Seoul (KR)

(73) Assignees: Hyundai Motor Company, Seoul (KR); Kia Motors Corporation, Seoul (KR); Sookmyung Women's University Industry-Academic Cooperation Foundation, Seoul (KR)

( * ) Notice: Subject to any disclaimer, the term of this patent is extended or adjusted under 35 U.S.C. 154(b) by 100 days.

(21) Appl. No.: 17/061,133

(22) Filed: Oct. 1, 2020

(65) Prior Publication Data

US 2021/0163033 A1 Jun. 3, 2021

(30) Foreign Application Priority Data

Dec. 3, 2019 (KR) .................. 10-2019-0158707

(51) Int. Cl.
*B60W 50/10* (2012.01)
*B60W 60/00* (2020.01)
*G06F 3/01* (2006.01)

(52) U.S. Cl.
CPC ........ *B60W 50/10* (2013.01); *B60W 60/0011* (2020.02); *G06F 3/015* (2013.01); *B60W 2540/22* (2013.01)

(58) Field of Classification Search
None
See application file for complete search history.

(56) References Cited

U.S. PATENT DOCUMENTS

2010/0010365 A1* 1/2010 Terao ............... A61B 5/369
600/544
2015/0265201 A1* 9/2015 Arbas .............. A61B 5/369
600/595

OTHER PUBLICATIONS

Seralynne, Vann "What does the retrosplenial cortex do?" Nov. 2009, Macmillion Publishers, p. 1-4, 12 (Year: 2009).*
C, Lin "EEG correlates of spatial orientation in the human retrosplenial complex" Jul. 9, 2015, Elsevier, p. 1-4 (Year: 2015).*
Yuanqing, Li, "Intelligent wheelchair based on multimode brain-machine interface (English)", Jan. 11, 2012, Machine English translation of CN 102309380 A (Year: 2012).*

* cited by examiner

Primary Examiner — James J Lee
Assistant Examiner — David Hatch
(74) *Attorney, Agent, or Firm* — Slater Matsil, LLP

(57) ABSTRACT

An apparatus for providing a customized mobility driving path using a brain wave signal includes a sensor configured to collect a brain wave signal for a driver of a mobility in a predetermined channel region, an analyzer configured to determine information to be provided regarding a planned path by analyzing the brain wave signal collected in the predetermined channel region, and a controller configured to control an operation of the mobility based on the information to be provided.

18 Claims, 8 Drawing Sheets

−9.3 μN      −0.6 μN

−1.8 μN      13.0 μN

APPARATUS AND METHOD FOR PROVIDING CUSTOMIZED MOBILITY DRIVING PATH USING BRAIN WAVE

CROSS-REFERENCE TO RELATED APPLICATIONS

This application claims priority to Korean Patent Application No. 10-2019-0158707, filed on Dec. 3, 2019, which application is hereby incorporated herein by reference.

TECHNICAL FIELD

The present disclosure relates to a mobility controlling method and apparatus.

BACKGROUND

The statements in this section merely provide background information related to the present disclosure and may not constitute prior art.

As one of the transport means, a vehicle (or mobility) is a very important means and tool for living a life in the modern world. Furthermore, a mobility itself may be regarded as something special that gives meaning to someone.

As technology is advanced, functions provided by a mobility also gradually evolve. For example, in recent years, mobilities not only transport a passenger to a destination, but also meet a passenger's needs for faster and safer travel to a destination. In addition, new devices are being added to a mobility system in order to satisfy a passenger's aesthetic taste and comfort. In addition, the existing devices like steering wheels, transmissions and acceleration/deceleration devices are also being developed so that more functions can be provided to users.

Meanwhile, a brain-computer interface or a brain-machine interface is a field of controlling a computer or a machine according to a person's intention by using brain wave signals. ERP (Event-Related Potential) is closely related to cognitive functions.

SUMMARY

The present disclosure relates to a mobility controlling method and apparatus. Particular embodiments relate to a mobility controlling method and apparatus based on error monitoring.

An embodiment of the present invention provides an apparatus and method for providing a customized mobility driving path based on a driver's brain wave signal.

Another embodiment of the present invention provides a customized mobility driving path providing apparatus and method that adjust an amount of information to be provided regarding a planned path by using a brain wave signal obtained from a predetermined region of a driver.

The embodiments of the present disclosure are not limited to the above-mentioned embodiments, and other embodiments that are not mentioned will be clearly understood by those skilled in the art through the following descriptions.

According to embodiments of the present invention, a customized mobility driving path providing apparatus using a brain wave signal may be provided which includes a sensor configured to collect a brain wave signal for a driver of a mobility in a predetermined channel region, an analyzer configured to determine information to be provided regarding a planned path by analyzing the brain wave signal collected from the predetermined channel region, and a controller configured to control an operation of the mobility on the basis of the information to be provided.

The predetermined channel region may include at least one of a first region including the hippocampus and a second region including the retrosplenial cortex.

The brain wave signal may be a brain wave signal in a time series plane.

The analysis may include comparing an amplitude of a brain wave signal collected in the predetermined channel region and a predetermined threshold.

The amplitude of the brain wave signal may be a power spectrum of the brain wave signal at a specific frequency.

The analysis may include comparing an amplitude of oxygen saturation collected in the predetermined channel region and a predetermined threshold.

The analyzer may classify a type for a planned path by analyzing a brain wave signal collected in the predetermined channel region and, on the basis of the classified type, determine information to be provided regarding the planned path.

The analyzer may classify a type for the planned path by analyzing an amplitude of a brain wave signal collected in the predetermined channel region and, on the basis of the classified type, adjust an amount of information to be provided regarding the planned path.

The analyzer may classify a type for the planned path by analyzing an amplitude of oxygen saturation collected in the predetermined channel region and, on the basis of the classified type, adjust an amount of information to be provided regarding the planned path.

When the predetermined channel region includes the first region and a first signal and a second signal larger than the first signal are collected in the first region, information to be provided in response to the second signal may have a larger amount than information to be provided in response to the first signal.

When the predetermined channel region includes the second region and a first signal and a second signal larger than the first signal are collected in the second region, information to be provided in response to the second signal may have a smaller amount than information to be provided in response to the first signal.

When the predetermined channel region includes the first region and the second region, the analyzer may ultimately determine information to be provided regarding the planned path by combining an analysis result for a brain wave signal collected in the first region and an analysis result for a brain wave signal collected in the second region.

The controller may adjust an amount of information provided by a predetermined apparatus included in the mobility, and the predetermined apparatus may include at least one of a steering apparatus, a pedal apparatus, a transmission, a video system, an audio system, a navigation system, and other mobility manipulation devices.

According to embodiments of the present invention, a customized mobility driving path providing method using a brain wave signal may be provided which includes collecting a brain wave signal for a driver of a mobility in a predetermined channel region, determining information to be provided regarding a planned path by analyzing the brain wave signal collected from the predetermined channel region, and controlling an operation of the mobility on the basis of the information to be provided.

The predetermined channel region may include at least one of a first region including the hippocampus and a second region including the retrosplenial cortex.

The brain wave signal may be a brain wave signal in a time series plane.

The analysis may include comparing an amplitude of a brain wave signal collected in the predetermined channel region and a predetermined threshold.

The amplitude of the brain wave signal may be a power spectrum of the brain wave signal at a specific frequency.

The analysis may include comparing an amplitude of oxygen saturation collected in the predetermined channel region and a predetermined threshold.

The determining of information to be provided regarding the planned path may include classifying a type for the planned path by analyzing a brain wave signal collected in the predetermined channel region and, on the basis of the classified type, determining information to be provided regarding the planned path.

The determining of information to be provided regarding the planned path may include classifying a type for the planned path by analyzing an amplitude of a brain wave signal collected in the predetermined channel region and, on the basis of the classified type, adjusting an amount of information to be provided regarding the planned path.

The determining of information to be provided regarding the planned path may include classifying a type for the planned path by analyzing an amplitude of oxygen saturation collected in the predetermined channel region and, on the basis of the classified type, adjusting an amount of information to be provided regarding the planned path.

When the predetermined channel region includes the first region and a first signal and a second signal larger than the first signal are collected in the first region, information to be provided in response to the second signal may have a larger amount than information to be provided in response to the first signal.

When the predetermined channel region includes the second region and a first signal and a second signal larger than the first signal are collected in the second region, information to be provided in response to the second signal may have a smaller amount than information to be provided in response to the first signal.

When the predetermined channel region includes the first region and the second region, the determining of information to be provided regarding the planned path may include ultimately determining information to be provided regarding the planned path by combining an analysis result for a brain wave signal collected in the first region and an analysis result for a brain wave signal collected in the second region.

The controlling of an operation of the mobility may adjust an amount of information provided by a predetermined apparatus included in the mobility, and the predetermined apparatus may include at least one of a steering apparatus, a pedal apparatus, a transmission, a video system, an audio system, a navigation system, and other mobility manipulation devices.

The features briefly summarized above with respect to embodiments of the present disclosure are merely exemplary aspects of the detailed description below of embodiments of the present disclosure, and do not limit the scope of the present disclosure.

According to embodiments of the present invention, an apparatus and method for providing a customized mobility driving path based on a driver's brain wave signal may be provided.

In addition, according to embodiments of the present invention, a customized mobility driving path providing apparatus and method may be provided which adjust an amount of information to be provided regarding a planned path by using a brain wave signal obtained from a predetermined region of a driver.

Effects obtained in embodiments of the present disclosure are not limited to the above-mentioned effects, and other effects not mentioned above may be clearly understood by those skilled in the art from the following description.

BRIEF DESCRIPTION OF THE DRAWINGS

In order that the disclosure may be well understood, there will now be described various embodiments thereof, given by way of example, reference being made to the accompanying drawings, in which.

DETAILED DESCRIPTION OF ILLUSTRATIVE EMBODIMENTS

Figure 1:
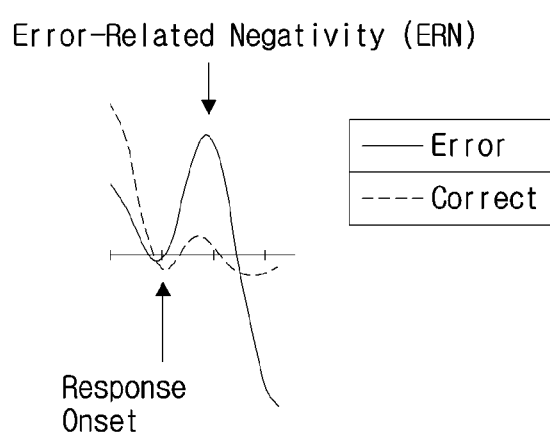
FIG. 1 is a view illustrating a general waveform of ERN in one embodiment of the present disclosure.

The following description is merely exemplary in nature and is not intended to limit the present disclosure, application, or uses. It should be understood that throughout the drawings, corresponding reference numerals indicate like or corresponding parts and features.

The following description is merely exemplary in nature and is not intended to limit the present disclosure, application, or uses. It should be understood that throughout the drawings, corresponding reference numerals indicate like or corresponding parts and features.

Exemplary embodiments of the present disclosure will be described in detail such that the ordinarily skilled in the art would easily understand and implement an apparatus and a method provided by embodiments of the present disclosure in conjunction with the accompanying drawings. However, the present disclosure may be embodied in various forms and the scope of the present disclosure should not be construed as being limited to the exemplary embodiments.

In describing embodiments of the present disclosure, well-known functions or constructions will not be described in detail when they may obscure the spirit of the present disclosure.

In embodiments of the present disclosure, it will be understood that when an element is referred to as being "connected to", "coupled to", or "combined with" another element, it can be directly connected or coupled to or combined with the another element or intervening elements may be present therebetween. It will be further understood that the terms "comprises", "includes", "have", etc. when used in embodiments of the present disclosure specify the presence of stated features, integers, steps, operations, elements, components, and/or combinations thereof but do not preclude the presence or addition of one or more other features, integers, steps, operations, elements, components, and/or combinations thereof.

It will be understood that, although the terms "first", "second", etc. may be used herein to describe various elements, these elements should not be limited by these terms. These terms are only used to distinguish one element from another element and are not used to show order or priority among elements. For instance, a first element discussed below could be termed a second element without departing from the teachings of the present disclosure. Similarly, the second element could also be termed as the first element.

In embodiments of the present disclosure, distinguished elements are termed to clearly describe features of various elements and do not mean that the elements are physically separated from each other. That is, a plurality of distinguished elements may be combined into a single hardware unit or a single software unit, and conversely one element may be implemented by a plurality of hardware units or software units. Accordingly, although not specifically stated, an integrated form of various elements or separated forms of one element may fall within the scope of the present disclosure. Also, the terms, such as 'unit' or 'module', etc., should be understood as a unit that processes at least one function or operation and that may be embodied in a hardware manner (e.g., a processor), a software manner, or a combination of the hardware manner and the software manner.

In embodiments of the present disclosure, all of the constituent elements described in various forms should not be construed as being essential elements but some of the constituent elements may be optional elements. Accordingly, embodiments configured by respective subsets of constituent elements in a certain form also may fall within the scope of the present disclosure. In addition, embodiments configured by adding one or more elements to various elements also may fall within the scope of the present disclosure.

As an electrical activity of neurons constituting a brain, a brain wave signal (or brain signal, brain wave) means a bio signal that directly and indirectly reflects a conscious or nonconscious state of a person. A brain wave signal can be measured in every area of human scalp, and its wavelength has a frequency of mainly 30 Hz or below and a potential difference of scores of microvolts. Depending on brain activity and state, various waveforms may appear. Research on interface control using a brain wave signal according to a person's intention is under way. A brain wave signal may be obtained by using EEG (Electro Encephalo Graphy) using electrical signals caused by brain activities, MEG (Magneto Encephalo Graphy) using magnetic signals occurring with electrical signals, and fMRI (functional Magnetic Resonance Imaging) or fNIRS (functional Near-Infrared Spectroscopy) using a change of oxygen saturation in the blood. Although fMRI and fNIRS are useful techniques for measuring brain activities, fMRI has a low time-resolution and fNIRS has a low spatial-resolution in general. Due to these limitations, EEG signals are mostly used by virtue of excellent portability and time-resolution.

A brain wave signal changes spatially and over time according to brain activity. As a brain wave signal is usually difficult to analyze and its waveform is not easy to visually analyze, various processing methods are proposed.

For example, according to the number of oscillations (frequency), brain wave signals may be classified based on frequency bands (power spectrum classification). The classification considers a measured brain wave signal as a linear sum of simple signals at each specific frequency, decomposes the signal into each frequency component and indicates a corresponding amplitude. A brain wave signal at each frequency may be obtained by using pre-processing normally for noise elimination, the Fourier transform into frequency domain, and a band-pass filter (BPF).

More particularly, according to frequency band, brain waves may be classified into delta, theta, alpha, beta and gamma waves. Delta waves are brain waves with a frequency of 3.5 Hz or below and an amplitude of 20~200 µV, mainly appearing in normal deep sleep or newborns. In addition, delta waves may increase as our awareness of the physical world decreases. Generally, theta waves are brain waves with a frequency of 3.5~7 Hz, mainly appearing in emotionally stable states or in sleep.

In addition, theta waves are generated mainly in the parietal cortex and in the occipital cortex and may appear during calm concentration for recollecting a memory or meditating. Generally, alpha waves are brain waves with a frequency of 8~12 Hz, mainly appearing in relaxed and comfortable states. In addition, alpha waves are normally generated in the occipital cortex during rest and may diminish in sleep. Generally, beta waves are brain waves with a frequency of 13~30 Hz, mainly appearing in a state of tension, which is bearable enough, or while a certain level of attention is paid. In addition, beta waves are mainly generated in the frontal cortex and are related to an awakened state or concentrated brain activities, pathological phenomena and medicinal effects. Beta waves may appear in a wide area throughout the brain. In addition, specifically, the beta waves may be divided into SMR waves with a frequency of 13~15 Hz, mid-beta waves with a frequency of 15~18 Hz and high beta waves with a frequency of 20 Hz and above. As beta waves appear to be stronger under stress like anxiety and tension, they are called stress waves. Gamma waves are brain waves that generally have a frequency of 30~50 Hz, mainly appearing in a strongly excited state or during high-level cognitive information processing. In addition, gamma waves may appear in an awaking state of consciousness and during REM sleep and may also be overlapped with beta waves.

Each of the brain wave signals according to frequency band is associated with a specific cognitive function. For example, delta waves are associated with sleep, theta waves are associated with working memory, and alpha waves are associated with attention or inhibition. Thus, the property of a brain wave signal at each frequency band selectively displays a specific cognitive function. In addition, the brain wave signal at each frequency band may show a little different aspect in each measuring part on the surface of the head. The cerebral cortex may be divided into frontal cortex, parietal cortex, temporal cortex and occipital cortex. These parts may have a few different roles. For example, the occipital cortex corresponding to the back of head has the primary visual cortex and thus can primarily process visual information. The parietal cortex located near the top of head has the somatosensory cortex and thus can process motor/ sensory information. In addition, the frontal cortex can process information related to memory and thinking, and the temporal cortex can process information related to auditory sense and olfactory sense.

Meanwhile, for another example, a brain wave signal may be analyzed by using ERP (Event-Related Potential). ERP is an electrical change in a brain in association with a stimulus from outside or a psychological process inside. ERP means a signal including an electrical activity of the brain, which is caused by a stimulus including specific information (for example, image, voice, sound, command of execution, etc.) after a certain time since the stimulus is presented.

To analyze an ERP, a process of separating a signal from a noise is desired. An averaging method may be mainly used. Particularly, by averaging brain waves measured based on stimulus onset time, it is possible to remove brain waves, which are not related to a stimulus, and to pick out only a related potential, that is, a brain activity commonly associated with stimulus processing.

As ERP has a high time resolution, it is closely related to research on cognitive function. ERP is an electrical phenomenon that is evoked by an external stimulus or is related to an internal state. According to types of stimuli, ERPs may be classified into auditory sense-related potentials, sight-related potentials, somatic sense-related potentials and olfactory sense-related potentials. According to properties of stimuli, ERPs may be classified into exogenous ERPs and endogenous ERPs. Exogenous ERPs have a waveform determined by an external stimulus, are related to automatic processing, and mainly appear in the initial phase of being given the stimulus. For example, exogenous ERPs are brainstem potentials. On the other hand, endogenous ERPs are determined by an internal cognitive process or a psychological process or state, irrespective of stimuli, and are related to 'controlled processing.' For example, endogenous ERPs are P300, N400, P600, CNV (Contingent Negative Variation), etc.

Names given to ERP peaks normally include a polarity and a latent period, and the peak of each signal has an individual definition and meaning. For example, the positive potential is P, the negative potential is N, and P300 means a positive peak measured about 300 ms after the onset of a stimulus. In addition, 1, 2, 3 or a, b, c and the like are applied according to the order of appearance. For example, P3 means a third positive potential in waveform after the onset of a stimulus.

Hereinafter, various ERPs will be described.

For example, Moo is related to a response to an unpredictable stimulus.

MMN (Mismatch Negativity) may be generated not only by a focused stimulus but also by a non-focused stimulus. MMN may be used as an indicator for whether or not a sense memory (echoic memory) operates before initial attention. P300, which will be described below, appears in a process of paying attention and making judgment, while MMN is analyzed as a process occurring in the brain before paying attention.

For another example, N200 (or N2) is mainly generated according to visual and auditory stimuli and is related to short-term memory or long-term memory, which are types of memories after attention, along with P300 described below.

For yet another example, P300 (or P3) mainly reflects attention to a stimulus, stimulus cognition, memory search and alleviation of uncertain feeling and is related to a perceptual decision distinguishing stimuli from outside. As the generation of P300 is related to a cognitive function, P300 is generated irrespective of types of presented stimuli. For example, P300 may be generated in auditory stimuli, visual stimuli and somatic stimuli. P300 is widely applied to research on the brain-computer interface.

For yet another example, N400 is related to language processing and is caused when a sentence or an auditory stimulus with a semantic error is presented. In addition, N400 is related to a memory process and may reflect a process of retrieving or searching information from long-term memory.

For yet another example, as an indicator showing reconstruction or recollective process, P600 is related to a process of processing a stimulus more accurately based on information stored in long-term memory.

For yet another example, CNV refers to potentials appearing for 200~300 ms and even for a few seconds in the later phase. It is also called slow potentials (SPs) and is related to expectancy, preparation, mental priming, association, attention and motor activity.

For yet another example, ERN (Error-Related Negativity) or Ne (error negativity) is an event-related potential (ERP) generated by a mistake or an error. It may occur when a subject makes a mistake in a sensorimotor task or a similar task. More particularly, when a subject cognizes a mistake or an error, ERN is generated and its negative peak appears mainly in the frontal and central zones for about 50~150 ms. Especially, it may appear in a situation where a mistake related to motor response is likely to occur, and may also be used to indicate a negative self-judgment.

Hereinafter, the major features of ERN will be described in more detail.

FIG. 1 is a view illustrating a general waveform of ERN according to one embodiment of the present disclosure.

Referring to FIG. 1, negative potential values are depicted above the horizontal axis, and positive potential values are depicted below the horizontal axis. In addition, it can be confirmed that an ERP with a negative peak value is generated within a predetermined time range after a response onset for an arbitrary motion. Herein, the response may mean a case where a mistake or an error is made (Error Response). In addition, the predetermined time range may be about 50~150 ms. Alternatively, the predetermined time range may be about 0~100 ms. Meanwhile, in the case of a correct response, an ERP is generated which has a relatively smaller negative peak than ERN.

As an ERP of initial negativity, ERN is time-locked until a response error occurs. In addition, ERN is known to reflect the reinforcement activity of a dopaminergic system related to behavioral monitoring. ERN includes the fronto-striatal loop including the rostral cingulate zone. Meanwhile, dopamine is associated with the reward system of brain that usually forms a specific behavior and motivates a person thereby providing pleasure and reinforced feelings. When a behavior obtaining an appropriate reward is repeated, it is learned as a habit. In addition, more dopamine is released through emotional learning, and a new behavior is attempted due to the release of dopamine. Thus, reward-driven learning is called reinforcement learning.

In addition, ERN may be generated in 0~100 ms after the onset of an erroneous response that is caused during an interference task (for example, Go-noGo task, Stroop task, Flanker task, and Simon task) through the frontal cortex lead.

In addition, together with CRN described below, ERN is known to reflect a general behavior monitoring system that can distinguish a right behavior and a wrong behavior.

In addition, the fact that ERN reaches a maximum amplitude at the frontal cortex electrode is known to reflect that an intracerebral generator is located in the rostral cingulate zone or the dorsal anterior cingulate cortex (dACC) zone.

In addition, ERN may show a change of amplitude according to a negative emotional state.

In addition, ERN may be reported even in a situation where behavioral monitoring is performed based on external evaluation feedback processing unlike internal motor expression, and may be classified as FRN described below.

In addition, ERN may be generated not only when having cognized a mistake or an error but also before cognizing the mistake or the error.

In addition, ERN may be generated not only as a response to his/her own mistake or error but also as a response to a mistake or error of others.

In addition, ERN may be generated not only as a response to a mistake or an error but also as a response to anxiety or stress for a predetermined performance task or object.

In addition, as a larger peak value of ERN is obtained, it may be considered as reflecting a more serious mistake or error.

Meanwhile, for yet another example, being an event-related potential (ERP) that is generated after ERN, Pe (Error Positivity) is an ERP with a positive value, which is generated mainly at the frontal cortex electrode in about 150~300 ms after a mistake or an error. Pe is known as a reaction that realizes a mistake or an error and pays more attention. In other words, Pe is related to an indicator of a conscious error information processing process after error detection. ERN and Pe are known as ERPs related to error monitoring.

Hereinafter, the major features of Pe will be described in more detail.

Figure 2:
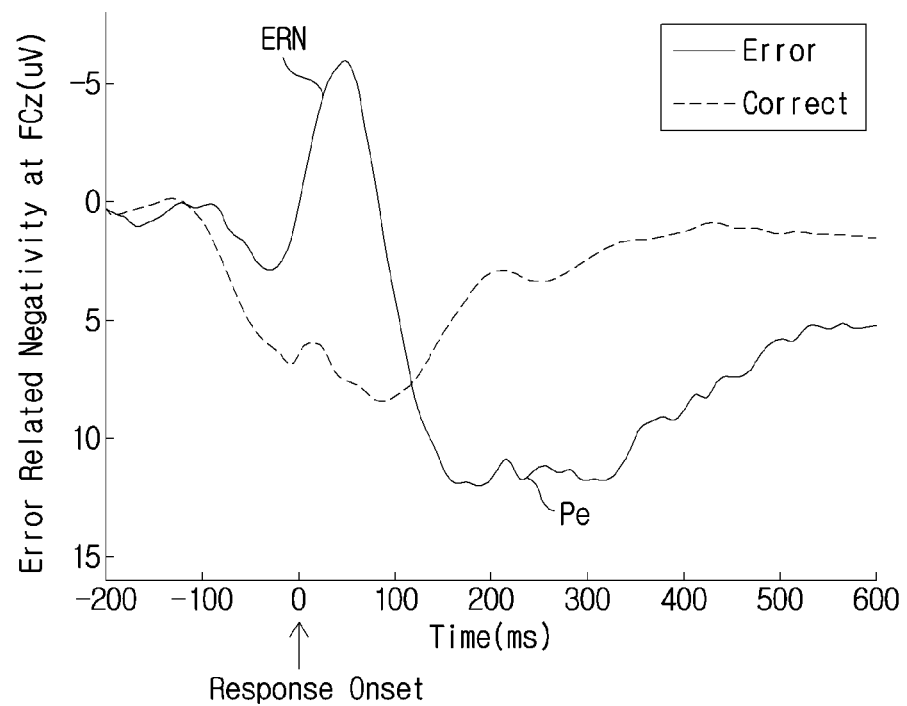
FIG. 2 is a view illustrating general waveforms of ERN and Pe according to one embodiment of the present disclosure.

FIG. 2 is a view illustrating general waveforms of ERN and Pe according to another embodiment of the present disclosure.

Referring to FIG. 2, negative potential values are depicted above positive potential values. In addition, it can be confirmed that an ERP with a negative peak value, that is an ERN, is generated within a first predetermined time range after a response onset for an arbitrary motion. Herein, the response may mean a case where a mistake or an error is made (Error Response). In addition, the first predetermined time range may be about 50~150 ms. Alternatively, the first predetermined time range may be about 0~200 ms.

In addition, it can be confirmed that an ERP with a positive peak value, that is a Pe, is generated within a second predetermined time range after the onset of the ERN. In addition, the second predetermined time range may be about 150~300 ms after an error onset. Alternatively, the second predetermined time range may mean about 200~400 ms.

Figure 3:
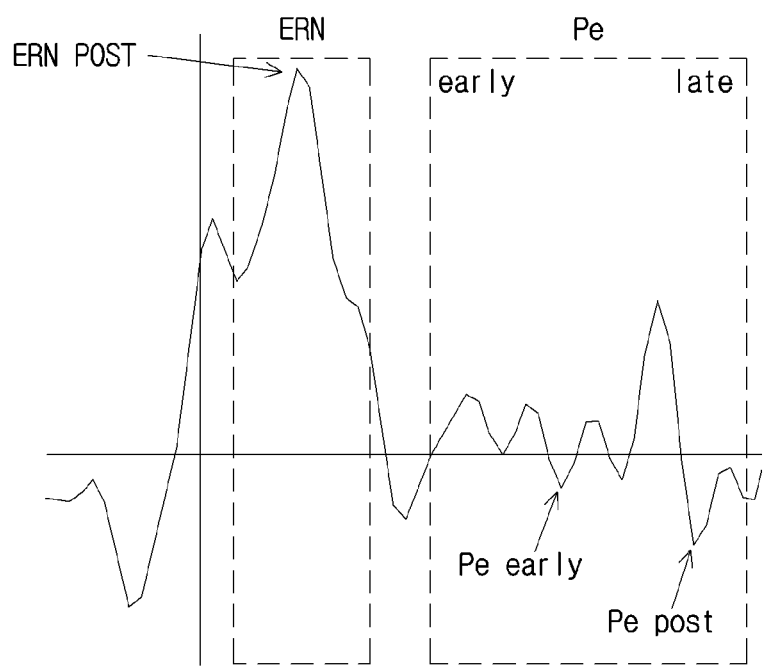
FIG. 3 is a view illustrating a deflection characteristic of Pe according to another embodiment of the present disclosure.

FIG. 3 is a view illustrating a deflection characteristic of Pe in one embodiment of the present disclosure.

Referring to FIG. 3, like P3, Pe has a wide deflection characteristic, and the plexus generator includes not only the areas of posterior cingulate cortex and insula cortex but also more anterior cingulate cortex.

In addition, Pe may reflect an emotional evaluation of an error and an attention to a stimulus like P300. In addition, ERN indicates a conflict between a right response and a wrong response, and Pe is known to be a response that realizes a mistake and pays more attention. In other words, ERN may be generated in a process of detecting a stimulus, and Pe may be generated depending on attention in a process of processing a stimulus. When ERN and/or Pe have relatively large values respectively, it is known that the values are related to an adaptive behavior intended to respond more slowly and more accurately after a mistake.

Figure 4A:
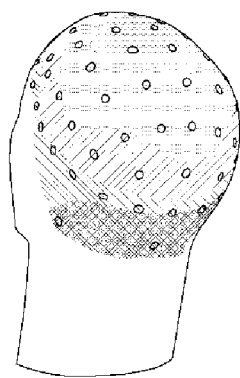
FIGS. 4A and 4B are views respectively illustrating measurement areas of ERP and Pe in one embodiment of the present disclosure.
Figure 4B:
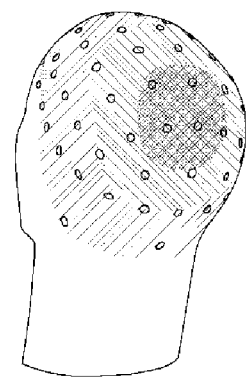

FIGS. 4A and 4B are views illustrating measurement areas of ERP and Pe according to one embodiment of the present disclosure.

ERN and Pe are known as ERPs related to error monitoring. Regarding the measurement areas of ERN and Pe, a largest negative value and a largest positive value may normally be measured in the central area. However, there may be a little difference according to measurement conditions. For example, FIG. 4A is the main area where ERN is measured, and the largest negative value of ERN may normally be measured in the midline frontal or central zone (that is, FCZ). In addition, FIG. 4B is the main area where Pe is measured, and a large positive value of Pe may normally be measured in a posterior midline zone as compared to ERN.

Meanwhile, for yet another example, FRN (Feedback-Related Negativity) is an event-related potential (ERP) that is related to error detection obtained based on external evaluation feedback. ERN and/or Pe detect an error based on an internal monitoring process. However, in the case of FRN, when being obtained based on external evaluation feedback, it may operate similarly to the process of ERN.

In addition, FRN and ERN may share many electrophysiological properties. For example, FRN has a negative peak value at the frontal cortex electrode in about 250~300 ms after the onset of a negative feedback and may be generated in the dorsal anterior cingulate cortex (dACC) zone like ERN.

In addition, like ERN, FRN may reflect an activity of reinforcement learning by a dopaminergic system. In addition, FRN normally has a larger negative value than a positive feedback and may have a larger value for an unforeseen case than for a predictable result.

Figure 5:
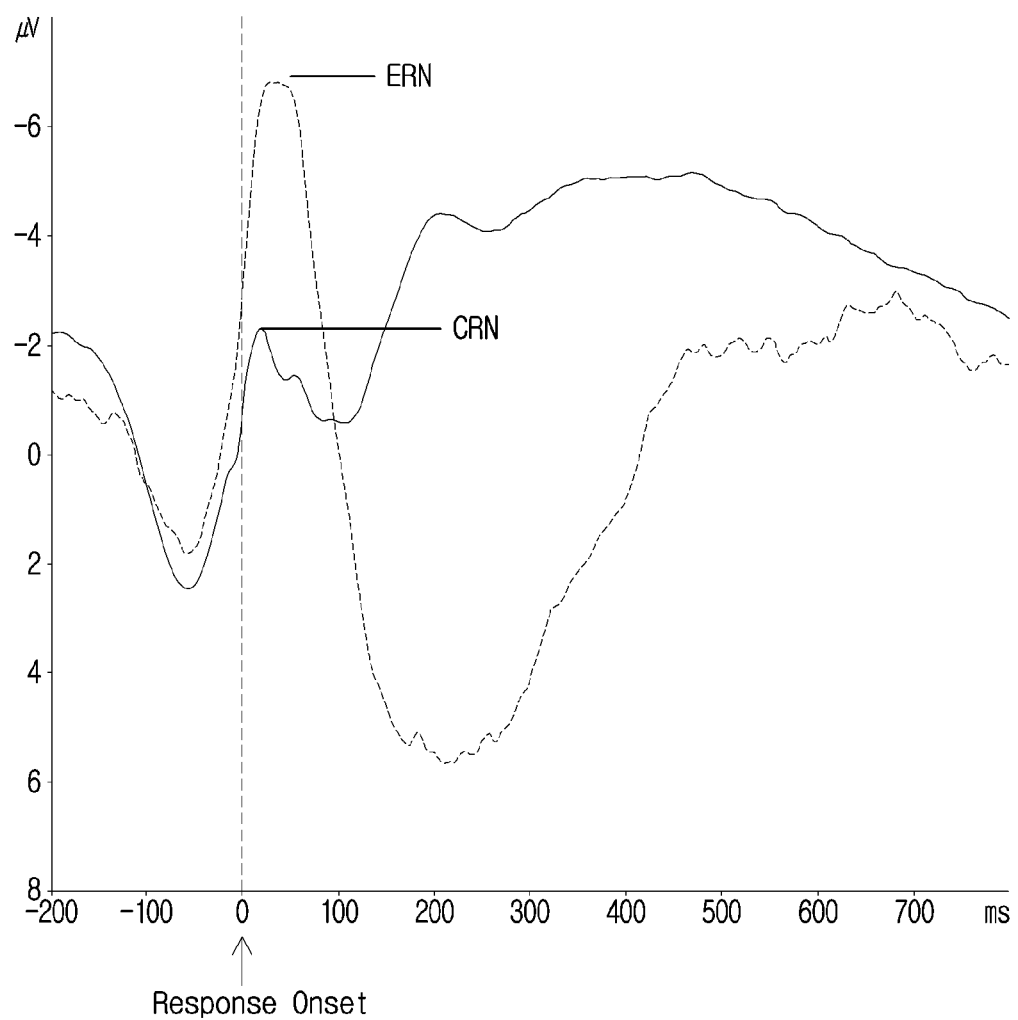
FIG. 5 is a view illustrating general waveforms of ERN and CRN according to one embodiment of the present disclosure.

For yet another example, CRN (Correct-Related Negativity) is an ERP generated by a correct trial and is a negative value that is smaller than ERN. Like ERN, CRN may be generated in the initial latent period (for example, 0~100 ms). FIG. 5 is a view illustrating general waveforms of ERN and CRN in one embodiment of the present disclosure.

For yet another example, Pc (Correct Positivity) is an event-related potential generated following CRN. It is an event-related potential generated in about 150~300 ms after the onset of correct response. The relation between CRN and Pc may be similar to the relation between ERN and Pe.

Meanwhile, ERPs may be classified into stimulus-locked ERPs and response-locked ERPs. The stimulus-locked ERPs and the response-locked ERPs may be divided according to criteria like evoking cause of ERP and response time. For example, an ERP evoked from a moment when a word or a picture is presented to a user from outside may be called a stimulus-locked ERP. In addition, for example, an ERP evoked from a moment when a user speaks or pushes a button may be called a response-locked ERP. Accordingly, based on the above-described criterion, in general, stimulus-locked ERPs are N100, N200, P2, P3, etc., and response-locked ERPs are ERN, Pe, CRN, Pc, FRN, etc.

Meanwhile, brain waves may be classified according to manifesting motives. Brain waves may be classified into spontaneous brain waves (spontaneous potentials) manifested by a user's will and evoked brain waves (evoked potentials) that are naturally manifested according to external stimuli irrespective of the user's will. Spontaneous brain waves may be manifested when a user moves on his/her own or imagines a movement, while evoked brain waves may be manifested by visual, auditory, olfactory and tactile stimuli, for example.

Meanwhile, brain wave signals may be measured in accordance with the International 10-20 system. The International 10-20 system determines measurement points of brain wave signals on the basis of the relationship between the location of an electrode and the cerebral cortex areas.

Figure 6:
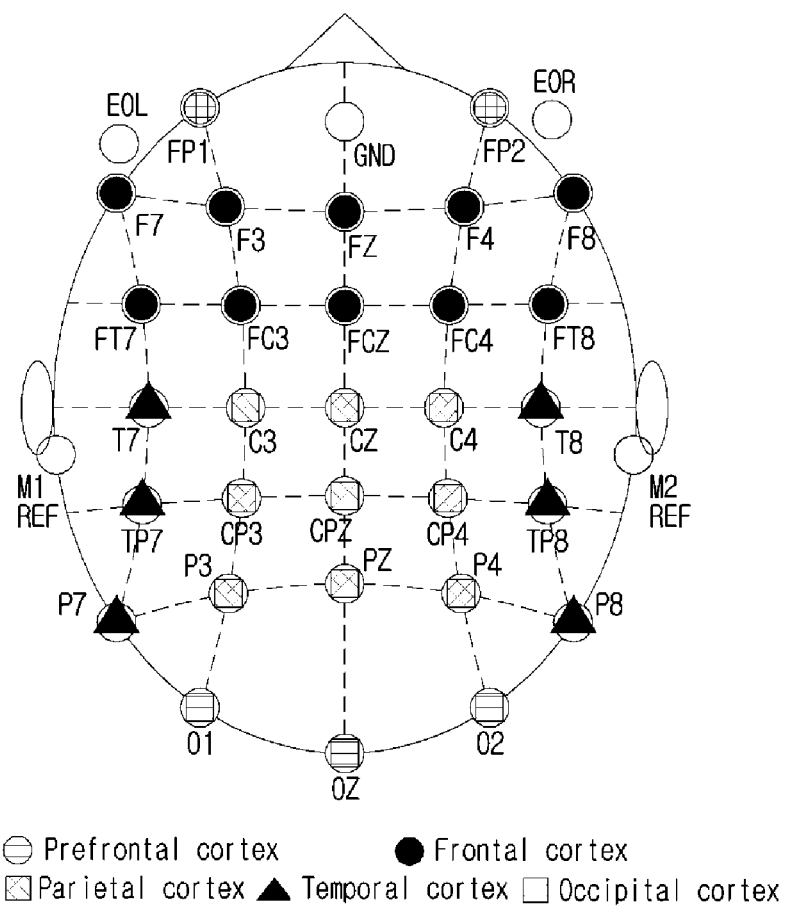
FIG. 6 is a view illustrating EEG measurement channels corresponding to cerebral cortex areas in one embodiment of the present disclosure.

FIG. 6 is a view illustrating EEG measurement channels corresponding to the cerebral cortex areas according to one embodiment of the present disclosure.

Referring to FIG. 6, brain areas (Prefrontal cortex FP1, FP2; Frontal cortex F3, F4, F7, F8, FZ, FC3, FC4, FT7, FT8, FCZ; Parietal cortex C3, C4, CZ, CP3, CP4, CPZ, P3, P4, PZ; Temporal cortex T7, T8, TP7, TP8, P7, P8; Occipital cortex O1, O2, OZ) correspond to 32 brain wave measurement channels. For each of the channels, data may be obtained and analysis may be performed for each cerebral cortex area by using the data.

Figure 7:
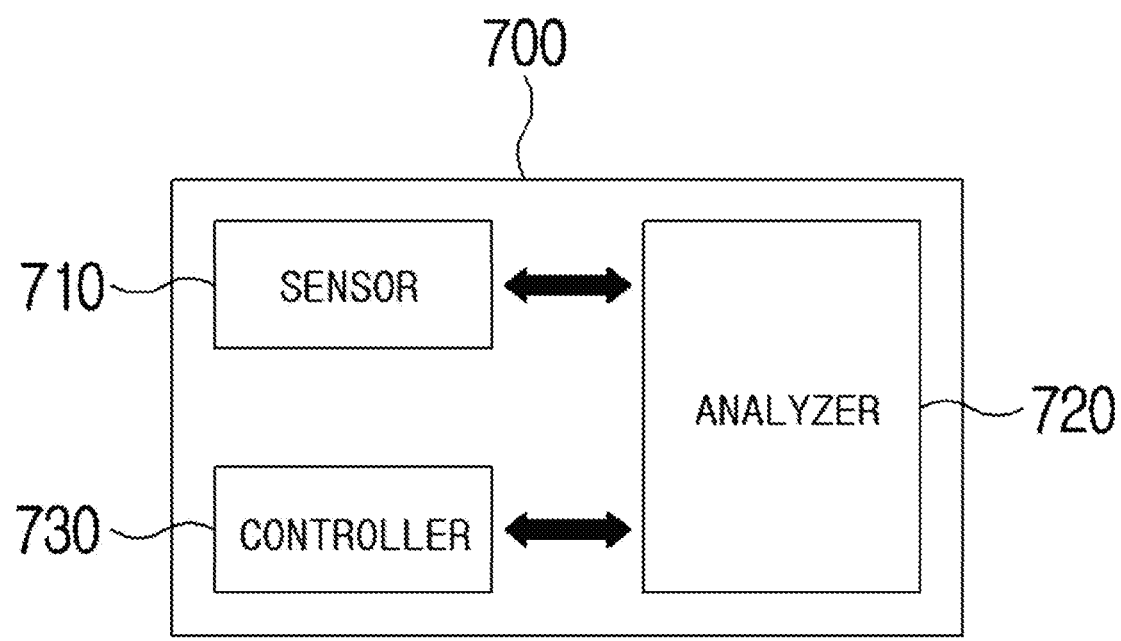
FIG. 7 is a block diagram illustrating a configuration of an apparatus for determining an amount of information to be provided to a driver in a mobility regarding a planned path on the basis of the driver's brain wave signal according to one embodiment of the present invention.

FIG. 7 is a block diagram illustrating a configuration of an apparatus for determining an amount of information to be provided to a driver in a mobility regarding a planned path on the basis of the driver's brain wave signal according to one embodiment of the present invention.

A fundamental purpose of a mobility is to bring a passenger to a destination. The recent technical advancement tends to produce various convenient functions available in mobilities, and more and more systems like navigation systems and autonomous driving systems appear to help drivers arrive at destinations more conveniently.

Meanwhile, the navigation systems and the autonomous driving systems provide uniform information irrespective of a driver and/or a path.

For example, a predetermined apparatus in a mobility usually provides a constant amount of information irrespective of a driver's proficiency. In other words, a constant amount of information is provided with no consideration for whether a driver is a new driver or an experienced driver.

For another example, a predetermined apparatus in a mobility provides a constant amount of information irrespective of a type of a planned path. In other words, a constant amount of information is provided with no consideration for whether a planned path is familiar or unfamiliar.

In addition, in order to modify an amount of information provided in a mobility, all the items in the setting of a corresponding apparatus should be changed manually.

Meanwhile, recent research has shown that different brain regions are involved depending on whether a path is familiar or unfamiliar. Particularly, it is known that whether a path is familiar or unfamiliar may be determined based on a brain wave signal measured in a hippocampus and/or in a retrosplenial cortex.

Herein, the hippocampus is a region located in the temporal lobe of the human brain and is known to be involved in learning new things. In addition, the hippocampus is known to be involved in driving to a newly known destination or along an unfamiliar path.

In addition, as the copus callosum is a nerve fiber bundle (white matter tract) connecting the right and left hemispheres and the splenial refers to the rear part of the corpus callosum, the retrosplenial cortex is known to be involved in learning about familiar things. In addition, the retrosplenial cortex is known to be involved in driving in a familiar place or path.

Accordingly, whether or not a driving path is familiar may be determined by analyzing an amplitude or activity of a brain wave signal from the hippocampus and/or the retrosplenial cortex.

Embodiments of the present disclosure may provide an apparatus and method for determining information to be provided to a driver in a mobility regarding a planned path on the basis of a brain wave signal generated from a predetermined region of the driver. In addition, embodiments of the present disclosure may provide an apparatus and method for controlling an operation of a mobility on the basis of the information to be provided.

Referring to FIG. 7, a customized mobility driving path providing apparatus 700 may include a sensor 710, an analyzer 720 and/or a controller 730. It should be noted, however, that only some of the components necessary for explaining the present embodiment are shown, and the components included in the customized mobility driving path providing apparatus 700 are not limited to the above-described example. For example, two or more constituent units may be implemented in one constituent unit, and an operation performed in one constituent unit may be divided and executed in two or more constituent units. Also, some of the constituent units may be omitted or additional constituent units may be added.

According to embodiments of the present disclosure, a customized mobility driving path providing apparatus and/or method using a brain wave signal may collect a brain wave signal for a driver of a mobility in a predetermined channel region. In addition, a customized mobility driving path providing apparatus of embodiments of the present disclosure may determine information to be provided regarding a planned path by analyzing the brain wave signal collected in the predetermined channel region. In addition, a customized mobility driving path providing apparatus of embodiments of the present disclosure may control an operation of the mobility on the basis of the information to be provided.

Particularly, the customized mobility driving path providing apparatus 700 of embodiments of the present disclosure may collect a brain wave signal for at least one passenger of a mobility in a predetermined channel region. In addition, the sensor 710 may perform the operation.

Here, the brain wave signal may mean a brain wave signal in a time series plane.

Here, the passenger may include a driver of the mobility.

In addition, the brain wave signal may mean a brain wave signal at each frequency. In addition, the brain wave signal may mean an amplitude of a brain wave signal at each frequency. In addition, the amplitude of the brain wave signal at each frequency may mean a power of a frequency band within a predetermined range. In other words, the amplitude of the brain wave signal at each frequency may mean a power that is obtained by converting, for example, measured signals by Fourier transform into a frequency band in a frequency domain.

In addition, the brain wave signal may include an oxygen saturation in a predetermined region.

Here, the predetermined channel region may include a region including a hippocampus and a region including a retrosplenial cortex.

In addition, a customized mobility driving path providing apparatus of the present disclosure may determine information to be provided regarding a planned path by analyzing the collected brain wave signal. In addition, the analyzer 720 may perform the operation.

Herein, the analysis may include comparing an amplitude of a brain wave signal collected in the predetermined channel region and a predetermined threshold. In addition, the analysis may include comparing an amplitude of a brain wave signal, which is collected for the predetermined time in a predetermined channel region, and a predetermined threshold. Here, the amplitude of the brain wave signal may mean a power spectrum of the brain wave signal at a specific frequency.

In addition, the analysis may include comparing an amplitude of oxygen saturation collected in the predetermined channel region and a predetermined threshold.

Here, the threshold may be a preset value or a value input by a user. In addition, the threshold may be different for each driver from whom a brain wave signal is collected. For example, it may be a value reflecting the brain wave signal characteristic of each driver. In order to reflect an analysis result of the brain wave signal characteristic, a predetermined learning process may be performed in advance for characteristics displayed in a driver's brain wave signal. In addition, the threshold may have multiple values.

Here, the threshold may be a statistical value of a brain wave signal for which prior learning is performed according to drivers.

Meanwhile, the analysis may include extracting a brain wave signal at each frequency.

In addition, a brain wave signal at each frequency that is used for the analysis may be a statistical value of a brain wave signal collected for a predetermined time. For example, the statistical value may mean an average value, a weighted average value, a maximum value and a minimum value.

In addition, the analysis may determine a driver's state from a point where an amplitude of a brain wave signal is equal to or greater than a predetermined threshold.

In addition, the analysis may determine a driver's state from a point where an amplitude of oxygen saturation in a predetermined region is equal to or greater than a predetermined threshold.

Herein, the analysis may include comparing an amplitude of a brain wave signal at each frequency, which is collected for the predetermined time, and a predetermined threshold.

Herein, the planned path may mean a path to a destination that a driver wants to reach, and the planned path may be set in a mobility. For example, a destination may be stored by a passenger's input in a navigation system.

Herein, the information to be provided regarding the planned path may include map information of the intended path, voice guidance information, and video guidance information. In addition, the information to be provided may include an amount of information to be provided to a driver.

For example, the information to be provided may include a size (scale) of a map provided in a navigation system, voice guidance information, guidance information on accident hazard zones, and guidance information on speed enforcement areas.

For another example, the information to be provided may include detailed guidance information given in an intricate path. Here, the intricate path may include a left-turn path, a right-turn path, detailed paths of intricate crossroads, and detailed paths of highway/motorway ramps and exits.

For yet another example, the information to be provided may include voice information given in a mobility. The voice information may include a volume and a direction.

Accordingly, a customized mobility driving path providing apparatus of embodiments of the present disclosure may adjust amounts of map information of a planned path, voice guidance information and video guidance information by analyzing the collected brain wave signal.

For example, when the collected brain wave signal is equal to or greater than a predetermined threshold, a size of a planned path map may be adjusted.

For another example, when the collected brain wave signal is equal to or greater than a predetermined threshold, a predetermined volume and direction of voice provided in a mobility may be adjusted.

For yet another example, when the collected brain wave signal is equal to or greater than a predetermined threshold, an amount of guidance information regarding accident hazard zones provided by a navigation system may be adjusted.

For yet another example, when an amplitude of oxygen saturation collected in a predetermined region is equal to or greater than a predetermined threshold, amounts of map information of a planned path, voice guidance information, and video guidance information may be adjusted.

In addition, a customized mobility driving path providing apparatus may adjust an amount of information to be provided regarding a planned path by analyzing a brain wave signal collected in a region including a hippocampus and/or a region including a retrosplenial cortex. In addition, a customized mobility driving path providing apparatus may adjust an amount of information to be provided regarding a planned path by analyzing an oxygen saturation collected in a region including a hippocampus and/or a region including a retrosplenial cortex.

Since a brain wave signal collected in a region including a hippocampus is involved in driving in an unfamiliar road, as an amplitude of a brain wave signal collected in the region is measured to be larger, a planned path may be stranger and more unfamiliar. Alternatively, a driver may be more inexperienced.

When a brain wave signal collected in a channel region including a hippocampus includes a first signal and a second signal that is larger than the first signal, information to be provided in response to the second signal may have a larger amount than information to be provided in response to the first signal. In other words, a path may be determined to be more unfamiliar in the case of the second signal than in the case of the first signal. Alternatively, a driver may be determined to be more inexperienced.

Here, the brain wave signal may mean an amplitude or a power spectrum of a brain wave signal. In addition, the amplitude of the brain wave signal may mean a power spectrum of the brain wave signal at a specific frequency.

Here, the first signal and the second signal may mean an amplitude or a power spectrum of the first signal and the second signal respectively. In addition, an amplitude of the first signal or an amplitude of the second signal may mean a power spectrum of the first signal and a power spectrum of the second signal at a specific frequency, respectively.

Herein, when a first signal is determined to be equal to or greater than a predetermined threshold, information to be provided in response to the first signal may mean information provided in a mobility on the basis of the determination result.

For example, a scale of a planned path map displayed on a navigation system monitor in response to the second signal may be larger than a scale of a planned path map displayed on the navigation system monitor in response to the first signal.

For another example, an amount of guidance information regarding accident hazard zones that is provided in a navigation system and a mobility black box in response to the second signal may be larger than an amount of guidance information regarding accident hazard zones that is displayed on a navigation system monitor in response to the first signal. Here, the guidance information regarding accident hazard zones may include speed bumps, black spots, children protection zones, falling rocks, foggy areas, wild animals signs, school zones, narrowing roads, downhill roads, an expressway under construction, bends, and a reminder for wearing a seat belt.

For yet another example, a volume of music provided in a mobility in response to the second signal may be lower than a volume of music provided in the mobility in response to the first signal. In other words, a volume of a sound other than voice information on a planned path may be reduced in order to make the voice information more audible.

Here, the first signal and the second signal may be equal to or greater than a predetermined threshold respectively.

On the other hand, since a brain wave signal collected in a region including a retrosplenial cortex is involved in driving along a familiar road, as an amplitude of a brain wave signal collected in the region is measured to be larger, a planned path may be more familiar and comfortable. Alternatively, a driver may be more experienced.

When a brain wave signal collected in a channel region including a retrosplenial cortex includes a first signal and a second signal that is larger than the first signal, information to be provided in response to the second signal may have a smaller amount than information to be provided in response to the first signal. In other words, a path may be determined to be more familiar in the case of the second signal than in the case of the first signal. Alternatively, a driver may be determined to be more experienced.

Herein, when a first signal is determined to be equal to or greater than a predetermined threshold, information to be provided in response to the first signal may mean information provided in a mobility on the basis of the determination result.

For example, a scale of a planned path map displayed on a navigation system monitor in response to the second signal may be smaller than a scale of a planned path map displayed on the navigation system monitor in response to the first signal.

For another example, an amount of guidance information regarding accident hazard zones that is provided in a navigation system and a mobility black box in response to the second signal may be smaller than an amount of guidance information regarding accident hazard zones that is displayed on a navigation system monitor in response to the first signal. Here, the guidance information regarding accident hazard zones may include speed bumps, black spots, children protection zones, falling rocks, foggy areas, wild animals signs, school zones, narrowing roads, downhill roads, an expressway under construction, bends, and a reminder for wearing a seat belt.

For yet another example, a volume of music provided in a mobility in response to the first signal may be lower than a volume of music provided in the mobility in response to the second signal. In other words, a volume of a sound other than voice information on a planned path may be reduced in order to make the voice information more audible.

Here, the first signal and the second signal may be equal to or greater than a predetermined threshold respectively.

In addition, a customized mobility driving path providing apparatus of embodiments of the present disclosure may ultimately adjust an amount of information to be provided regarding a planned path by combining an analysis result for a brain wave signal collected in a region including a hippocampus and an analysis result for a brain wave signal collected in a region including a retrosplenial cortex.

For example, a customized mobility driving path providing apparatus of embodiments of the present disclosure may provide a larger amount of information than information to be provided regarding a planned path in a navigation system, when an amplitude of a brain wave signal collected in a region including a hippocampus is equal to or larger than an amplitude of a brain wave signal collected in a region including a retrosplenial cortex.

For another example, a customized mobility driving path providing apparatus of embodiments of the present disclosure may provide a smaller amount of information than information to be provided regarding a planned path in a navigation system, when an amplitude of a brain wave signal collected in a region including a hippocampus is smaller than an amplitude of a brain wave signal collected in a region including a retrosplenial cortex.

Herein, the information to be provided in the navigation system may be a value preset by a user input or a mobility.

In addition, a customized mobility driving path providing apparatus of embodiments of the present disclosure may classify a type for a planned path by analyzing the brain wave signal collected in a predetermined channel region and determine information to be provided regarding the planned path on the basis of the classified type.

For example, a customized mobility driving path providing apparatus of embodiments of the present disclosure may classify a type for a planned path by analyzing an amplitude of a brain wave signal collected in a predetermined channel region and determine an amount of information to be provided regarding the planned path on the basis of the classified type.

Here, a type for the planned path may be represented by multiple phases. For example, the type may include a first type, a second type, . . . , a n-th type (n is an integer larger than 0).

Table 1 is an example showing a type for a planned path and an amount of information to be provided based on the type.

TABLE 1

| Threshold | Type | Information to be provided |
|---|---|---|
| First threshold | First type | First information |
| Second threshold | Second type | Second information |
| Third threshold | Third type | Third type |
| ... | ... | ... |

Referring to Table 1, the type may be classified using a multiplicity of thresholds. For example, a brain wave signal that is equal to or greater than a first threshold may be classified as a first type. In addition, when a brain wave signal that is equal to or greater than a second threshold and is smaller than a first threshold, it may be classified as a second type. Here, the first threshold may be highest, followed by the second threshold and the third threshold (first threshold>second threshold>third threshold).

In addition, the information to be provided may be determined based on the type. For example, in the case of the first type, the first information may be provided.

In addition, amounts of information to be provided may be in a sequential order. For example, the first information may have a largest amount, followed by the second information and the third information (first information>second information>third information). Alternatively, the third information may have a largest amount, followed by the second information and the first information (third information>second information>first information).

The customized mobility driving path providing apparatus 700 of embodiments of the present disclosure may control an operation of the mobility on the basis of the information to be provided. In addition, the controller 730 may perform the operation.

Here, the mobility may include a predetermined apparatus. For example, the predetermined apparatus may include a steering apparatus, a pedal apparatus (an accelerator pedal, a brake pedal), a transmission, a video system, an audio system, a navigation system, and other mobility manipulation apparatuses.

As described above, each apparatus of the mobility for providing information to be provided may be controlled depending on an amount of the information. In other words, controlling an operation of the mobility may mean adjusting an amount of information provided in a predetermined apparatus included in the mobility.

For example, an operation of a navigation display and a voice apparatus may be changed to be different from an existing setting.

For another example, an operation of a mobility black box may be changed to be different from an existing setting.

For yet another example, an operation of a voice apparatus provided in a mobility may be changed to be different from an existing setting.

Here, the existing setting may be a value preset by a user input or a mobility.

Meanwhile, a customized mobility driving path providing apparatus of the present disclosure may determine information to be provided regarding a planned path by analyzing a driver's brain wave signal. Thus, while controlling the mobility, the customized mobility driving path providing apparatus may update a predetermined threshold used for the analysis. In other words, the driver's brain wave signal, an amount of information to be provided, a mobility controlling operation and/or a preset threshold may be added as learning data for setting a value of the predetermined threshold.

Figure 8:
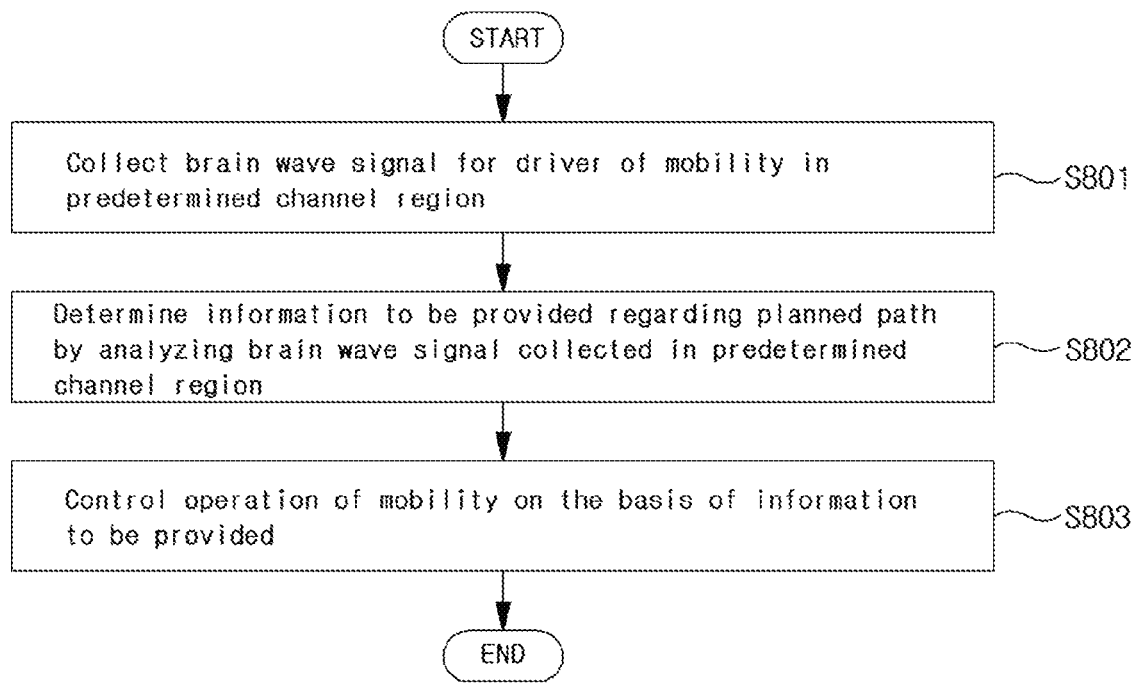
FIG. 8 is a flowchart illustrating a method of operating a customized mobility driving path providing apparatus according to one embodiment of the present invention.

FIG. 8 is a flowchart illustrating a method of operating a customized mobility driving path providing apparatus according to one embodiment of the present invention.

In the step S801, a brain wave signal for a driver in a mobility may be collected in a predetermined channel region.

Here, the predetermined channel region may include at least one of a first region including a hippocampus and a second region including a retrosplenial cortex.

Here, in addition, the brain wave signal may be a brain wave signal in a time series plane.

In the step S802, information to be provided regarding a planned path may be determined by analyzing the brain wave signal collected in the predetermined channel region.

Herein, the analysis may include comparing an amplitude of the brain wave signal collected in the predetermined channel region and a predetermined threshold. In addition, the analysis may include comparing an amplitude of oxygen saturation collected in the predetermined channel region and a predetermined threshold.

The determining of information to be provided regarding the planned path may mean classifying a type for the planned path by analyzing a brain wave signal collected in the predetermined channel region and, on the basis of the classified type, determining information to be provided regarding the planned path.

In addition, the determining of information to be provided regarding the planned path may mean classifying a type for the planned path by analyzing an amplitude of a brain wave signal collected in the predetermined channel region and, on the basis of the classified type, adjusting an amount of information to be provided regarding the planned path.

In addition, the determining of information to be provided regarding the planned path may mean classifying a type for the planned path by analyzing an amplitude of oxygen saturation collected in the predetermined channel region and, on the basis of the classified type, adjusting an amount of information to be provided regarding the planned path.

In addition, when the predetermined channel region includes the first region and the second region, the determining of information to be provided regarding the planned path may mean ultimately determining information to be provided regarding the planned path by combining an analysis result for a brain wave signal collected in the first region and an analysis result for a brain wave signal collected in the second region.

Meanwhile, when the predetermined channel region includes the first region and a first signal and a second signal larger than the first signal are collected in the first region, information to be provided in response to the second signal may have a larger amount than information to be provided in response to the first signal.

In addition, when the predetermined channel region includes the second region and a first signal and a second signal larger than the first signal are collected in the second region, information to be provided in response to the second signal may have a smaller amount than information to be provided in response to the first signal.

In the step S803, an operation of the mobility may be controlled based on the information to be provided.

Herein, controlling an operation of the mobility may mean adjusting an amount of information provided in a predetermined apparatus included in the mobility.

In addition, the predetermined apparatus may include at least one of a steering apparatus, a pedal apparatus, a transmission, a video system, an audio system, a navigation system, and other mobility manipulation apparatuses.

Effects obtained in embodiments of the present disclosure are not limited to the above-mentioned effects, and other effects not mentioned above may be clearly understood by those skilled in the art from the foregoing description.

Although exemplary methods of embodiments of the present disclosure are described as a series of operation steps for clarity of a description, the present disclosure is not limited to the sequence or order of the operation steps described above. The operation steps may be simultaneously performed, or may be performed sequentially but in different order. In order to implement the method of an embodiment of the present disclosure, additional operation steps may be added and/or existing operation steps may be eliminated or substituted.

Various embodiments of the present disclosure are not presented to describe all of the available combinations but are presented to describe only representative combinations. Steps or elements in various forms may be separately used or may be used in combination.

In addition, various embodiments of the present disclosure may be embodied in the form of hardware, firmware, software, or a combination thereof. When an embodiment of the present disclosure is embodied in a hardware component, it may be, for example, an application specific integrated circuit (ASIC), a digital signal processor (DSP), a digital signal processing device (DSPD), a programmable logic device (PLD), a field programmable gate array (FPGA), a general processor, a controller, a microcontroller, a microprocessor, etc.

The scope of the present disclosure includes software or machine-executable instructions (for example, operating systems (OS), applications, firmware, programs) that enable methods of various forms to be executed in an apparatus or on a computer, and a non-transitory computer-readable medium storing such software or machine-executable instructions so that the software or instructions can be executed in an apparatus or on a computer.

The description of embodiments of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. An apparatus for providing a customized mobility driving path using a brain wave signal, the apparatus comprising:
a sensor configured to collect a brain wave signal for a driver of a mobility in a predetermined channel region;
an analyzer configured to compare an amplitude of a brain wave signal collected in the predetermined channel region with a predetermined threshold, and determine information to be provided regarding a planned path by analyzing the brain wave signal collected in the predetermined channel region based on a result of the comparison;
wherein, when the amplitude of the brain wave signal collected in a first region is greater than or equal to a predetermined threshold, the analyzer is configured to determine that the driver of the mobility is in an inexperienced state with respect to the driving path and to determine information to be provided regarding the planned path based on the inexperienced state; and
wherein, when the amplitude of the brain wave signal collected in a second region different from the first region is greater than or equal to a predetermined threshold, the analyzer is configured to determine that the driver of the mobility is in an experienced state with respect to the driving path and determine information to be provided regarding the planned path based on the experienced state; and
a controller configured to control an operation of the mobility based on the information to be provided.

2. An apparatus for providing a customized mobility driving path using a brain wave signal, the apparatus comprising:
a sensor configured to collect a brain wave signal for a driver of a mobility in a predetermined channel region;
an analyzer configured to compare an amplitude of a brain wave signal collected in the predetermined channel region with a predetermined threshold, and determine information to be provided regarding a planned path by analyzing the brain wave signal collected in the predetermined channel region based on a result of the comparison;
wherein, when the amplitude of the brain wave signal collected in a first region is greater than or equal to a predetermined threshold, the analyzer is configured to determine that the driver of the mobility is in an inexperienced state with respect to the driving path and to determine information to be provided regarding the planned path based on the inexperienced state; and
wherein, when the amplitude of the brain wave signal collected in a second region different from the first region is greater than or equal to a predetermined threshold, the analyzer is configured to determine that the driver of the mobility is in an experienced state with respect to the driving path and determine information to be provided regarding the planned path based on the experienced state, wherein the first region comprises a hippocampus and the second region comprises a retrosplenial cortex; and
a controller configured to control an operation of the mobility based on the information to be provided.

3. The apparatus of claim 2, wherein, when the predetermined channel region comprises the first region and the second region, the analyzer is configured to ultimately determine the information to be provided regarding the planned path by combining an analysis result for a brain wave signal collected in the first region and an analysis result for a brain wave signal collected in the second region.

4. The apparatus of claim 1, wherein the analyzer is configured to classify a type for the planned path by analyzing the brain wave signal collected in the predetermined channel region and determine the information to be provided regarding the planned path based on the classified type.

5. The apparatus of claim 1, wherein the analyzer is configured to classify a type for the planned path by analyzing an amplitude of the brain wave signal collected in the predetermined channel region and adjust an amount of the information to be provided regarding the planned path based on the classified type.

6. The apparatus of claim 1, wherein the analyzer is configured to classify a type for the planned path by analyzing an amplitude of oxygen saturation collected in the predetermined channel region and adjust an amount of the information to be provided regarding the planned path based on the classified type.

7. The apparatus of claim 1, wherein:
the controller is configured to adjust an amount of the information provided in a predetermined apparatus in the mobility; and
the predetermined apparatus comprises at least one of a steering apparatus, a pedal apparatus, a transmission, a video system, an audio system, a navigation system, or other mobility manipulation apparatus.

8. A method for providing a customized mobility driving path using a brain wave signal, the method comprising:
collecting a brain wave signal for a driver of a mobility in a predetermined channel region;
comparing an amplitude of a brain wave signal collected in the predetermined channel region with a predetermined threshold;
determining information to be provided regarding a planned path by analyzing the brain wave signal collected in the predetermined channel region based on a result of the comparison; and
controlling an operation of the mobility based on the information to be provided;
wherein, when the amplitude of the brain wave signal collected in a first region is greater than or equal to a predetermined threshold, the analyzer is configured to determine that the driver of the mobility is in an inexperienced state with respect to the driving path and to determine information to be provided regarding the planned path based on the inexperienced state; and
wherein, when the amplitude of the brain wave signal collected in a second region different from the first region is greater than or equal to a predetermined threshold, the analyzer is configured to determine that the driver of the mobility is in an experienced state with respect to the driving path and determine information to be provided regarding the planned path based on the experienced state.

9. The method of claim 8, wherein the first region comprises a hippocampus and the second region comprises a retrosplenial cortex.

10. The method of claim 9, wherein, when the predetermined channel region comprises the first region and the second region, determining the information to be provided regarding the planned path comprises ultimately determining the information to be provided regarding the planned path by combining an analysis result for a brain wave signal collected in the first region and an analysis result for a brain wave signal collected in the second region.

11. The method of claim 8, wherein determining the information to be provided regarding the planned path comprises:
classifying a type for the planned path by analyzing the brain wave signal collected in the predetermined channel region; and
based on the classified type, determining the information to be provided regarding the planned path.

12. The method of claim 8, wherein determining the information to be provided regarding the planned path comprises:
classifying a type for the planned path by analyzing an amplitude of the brain wave signal collected in the predetermined channel region; and
based on the classified type, adjusting an amount of the information to be provided regarding the planned path.

13. The method of claim 8, wherein determining the information to be provided regarding the planned path comprises:
classifying a type for the planned path by analyzing an amplitude of oxygen saturation collected in the predetermined channel region; and
based on the classified type, adjusting an amount of the information to be provided regarding the planned path.

14. The method of claim 8, wherein:
controlling the operation of the mobility comprises adjusting an amount of the information provided in a predetermined apparatus in the mobility; and
the predetermined apparatus comprises at least one of a steering apparatus, a pedal apparatus, a transmission, a video system, an audio system, a navigation system, or other mobility manipulation apparatus.

15. The apparatus of claim 2, wherein the analyzer is configured to compare an amplitude of the brain wave signal collected in the predetermined channel region and a predetermined threshold to determine the information to be provided.

16. The apparatus of claim 2, wherein the analyzer is configured to classify a type for the planned path by analyzing the brain wave signal collected in the predetermined channel region and determine the information to be provided regarding the planned path based on the classified type.

17. The apparatus of claim 2, wherein the analyzer is configured to classify a type for the planned path by analyzing an amplitude of the brain wave signal collected in the predetermined channel region and adjust an amount of the information to be provided regarding the planned path based on the classified type.

18. The apparatus of claim 2, wherein the analyzer is configured to classify a type for the planned path by analyzing an amplitude of oxygen saturation collected in the predetermined channel region and adjust an amount of the information to be provided regarding the planned path based on the classified type.

* * * * *